US007826896B2

(12) United States Patent
Wang

(10) Patent No.: US 7,826,896 B2
(45) Date of Patent: Nov. 2, 2010

(54) METHOD AND APPARATUS FOR IMPEDANCE SIGNAL LOCALIZATIONS FROM IMPLANTED DEVICES

(75) Inventor: Li Wang, White Bear Township, MN (US)

(73) Assignee: Medtronic, Inc., Minneapolis, MN (US)

(*) Notice: Subject to any disclaimer, the term of this patent is extended or adjusted under 35 U.S.C. 154(b) by 791 days.

(21) Appl. No.: 11/555,918

(22) Filed: Nov. 2, 2006

(65) Prior Publication Data

US 2007/0118042 A1    May 24, 2007

Related U.S. Application Data

(62) Division of application No. 10/423,118, filed on Apr. 25, 2003, now Pat. No. 7,149,573.

(51) Int. Cl.
*A61B 5/05* (2006.01)

(52) U.S. Cl. .................. 600/547; 600/301; 600/512

(58) Field of Classification Search ......... 600/300–301, 600/309, 547, 512, 584
See application file for complete search history.

(56) References Cited

U.S. PATENT DOCUMENTS

| 5,501,702 | A | * | 3/1996 | Plicchi et al. ............... 607/20 |
| 5,562,711 | A |  | 10/1996 | Yerich et al. |
| 5,755,742 | A | * | 5/1998 | Schuelke et al. .............. 607/27 |
| 6,070,100 | A |  | 5/2000 | Bakels et al. |
| 6,473,640 | B1 |  | 10/2002 | Erlebacher |
| 6,512,949 | B1 |  | 1/2003 | Combs et al. |
| 6,684,101 | B2 |  | 1/2004 | Daum |
| 7,313,434 | B2 | * | 12/2007 | Belalcazar et al. .......... 600/547 |
| 2002/0002389 | A1 | * | 1/2002 | Bradley et al. ................ 607/8 |
| 2002/0107551 | A1 | * | 8/2002 | Stahmann et al. .............. 607/9 |

FOREIGN PATENT DOCUMENTS

EP    1348375    1/2003

* cited by examiner

*Primary Examiner*—Max Hindenburg
*Assistant Examiner*—Rene Towa
(74) *Attorney, Agent, or Firm*—Michael C. Soldner

(57) ABSTRACT

Method and apparatus for monitoring a plurality of physiological factors contributing to physiological conditions of a heart, that determines a first impedance, corresponding to the plurality of physiological factors, across a plurality of vectors, and a second impedance, corresponding to the plurality of physiological factors, across the plurality of vectors subsequent to determining the first impedance. A relative change in impedance corresponding to the plurality of vectors is determined in response to the first impedance and the second impedance, first minimally contributing physiological factors of the plurality of physiological factors associated with a first physiological factor of the plurality of physiological factors are determined, and relative change in tissue resistivity corresponding to the first physiological factor in response to physiological factors of the plurality of physiological factors other than the first minimal contributing physiological factors and the relative change in impedance are determined.

19 Claims, 5 Drawing Sheets

Susceptibility Matrix

| Vector # | Vector | Lung (ρ) αL (Ω) | Blood (ρ) αB (Ω) | Heart Muscle (ρ) αHM (Ω) | Skeletal Muscle (ρ) αSM (Ω) | Heart Volume αHV (Ω) | Lung Volume αLV (Ω) |
|---|---|---|---|---|---|---|---|
| 1 | RVC-Can/RVC-C | 0.14 | 0.13 | 0.021 | 0.37 | -0.0081 | 0.049 |
| 2 | Vr-C RVC-C | 0.14 | 0.023 | 0.020 | 0.37 | -0.0081 | 0.047 |
| 3 | Vr-C/Vr-C | 0.16 | 1.28 | 0.46 | 0.33 | -0.0078 | 0.050 |
| 4 | Vr-C/Vt-C | 0.15 | 0.035 | 0.023 | 0.33 | -0.0052 | 0.046 |
| 5 | RVC-C/RVC-B1 | 0.14 | 0.13 | 0.02 | 0.04 | -0.0081 | 0.049 |
| 6 | Vr-Ar/Vt-At | 0.025 | 0.10 | 0.015 | 0.002 | -0.025 | 0.003 |
| 7 | Ar-C/At-C | 0.15 | 0.034 | 0.023 | 0.33 | -0.052 | 0.003 |

FIG. 4

METHOD AND APPARATUS FOR IMPEDANCE SIGNAL LOCALIZATIONS FROM IMPLANTED DEVICES

CROSS-REFERENCE TO RELATED APPLICATION

This is a divisional application of and claims priority to U.S. Ser. No. 10/423,118 filed Apr. 25, 2003 now U.S. Pat No. 7,149,573, entitled "METHOD AND APPARATUS FOR IMPEDANCE SIGNAL LOCALIZATIONS FROM IMPLANTED DEVICES", incorporated herein by reference in its entirety.

FIELD OF THE INVENTION

The present invention relates generally to implantable medical devices (IMDs), and more particularly, the present invention relates to an apparatus and method for identifying cardiac insult using comparisons of multiple impedance vectors to differentiate between the physiological factors that contribute to cardiac insult.

BACKGROUND OF THE INVENTION

The impedance measuring vectors or paths provided by some modern pacemakers and implantable cardio defibrillators are quite extensive. Many pacemakers currently measure impedance to measure minute ventilation as a physiological indicator of activity. The minute ventilation value obtained in this way can be used to set the pacing rate in a physiological adaptive pacemaker. The impedance changes over time over a particular vector can have many contributing factors, some major and some minor, so that multiple factors contribute to impedance signals measured by the device. A nonexclusive list of such contributing factors in which changes in the factors over time can cause changes in the measured impedance over time across a vector include, for example, changes in lung resistivity, changes in blood resistivity, changes in heart muscle resistivity, changes in skeletal muscle resistivity, changes in heart volume, and changes in lung volume. Measuring changes in impedance or resistivity in a certain contributing factor can be problematic, since such changes tend to be relatively accurately detectable across one vector while being less susceptible to accurate detection across another vector. Some vectors are highly sensitive or susceptible to changes in certain of the contributing factors, while being less sensitive or susceptible to impedance changes in other contributing factors.

What is needed is a method and apparatus that more accurately differentiates between the multiple sources of and/or physiological factors that contribute to changes in impedance measures over time.

SUMMARY OF THE INVENTION

The present invention is directed to a method and apparatus for monitoring a plurality of physiological factors contributing to physiological conditions of a patient in an implantable medical device. According to an embodiment of the present invention, a first impedance, corresponding to the plurality of physiological factors, is determined across a plurality of vectors, and a second impedance, corresponding to the plurality of physiological factors, is determined across the plurality of vectors subsequent to determining the first impedance. A relative change in impedance corresponding to the plurality of vectors is determined in response to the first impedance and the second impedance, and first minimally contributing physiological factors of the plurality of physiological factors associated with a first physiological factor of the plurality of physiological factors are determined. Relative change in tissue resistivity corresponding to the first physiological factor is then determined in response to physiological factors of the plurality of physiological factors other than the first minimal contributing physiological factors and the relative change in impedance.

According to another embodiment of the present invention, an implantable medical device adapted to be implanted within a patient includes a housing portion housing electrical circuitry for operating the implantable medical device, and a plurality of electrodes positioned within the patient. A microprocessor determines a relative change in impedance corresponding to a plurality of vectors formed between the plurality of electrodes, determines first minimally contributing physiological factors of a plurality of physiological factors associated with a first physiological factor of a plurality of physiological factors, and determines relative change in resistivity corresponding to the first physiological factor in response to physiological factors of the plurality of physiological factors other than the first minimal contributing physiological factors and the relative change in impedance.

BRIEF DESCRIPTION OF THE DRAWINGS

Other advantages and features of the present invention will be readily appreciated as the same becomes better understood by reference to the following detailed description when considered in connection with the accompanying drawings, in which like reference numerals designate like parts throughout the figures thereof and wherein:

FIG. 4 is a table of sensitivity or susceptibility coefficients of several vectors to changes in impedance in several physiological factor impedance contributors.

DETAILED DESCRIPTION OF THE PREFERRED EMBODIMENTS

The following detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described above are merely for illustrative purposes, and are not intended to limit scope of the invention as defined in the claims that follow.

Figure 1:
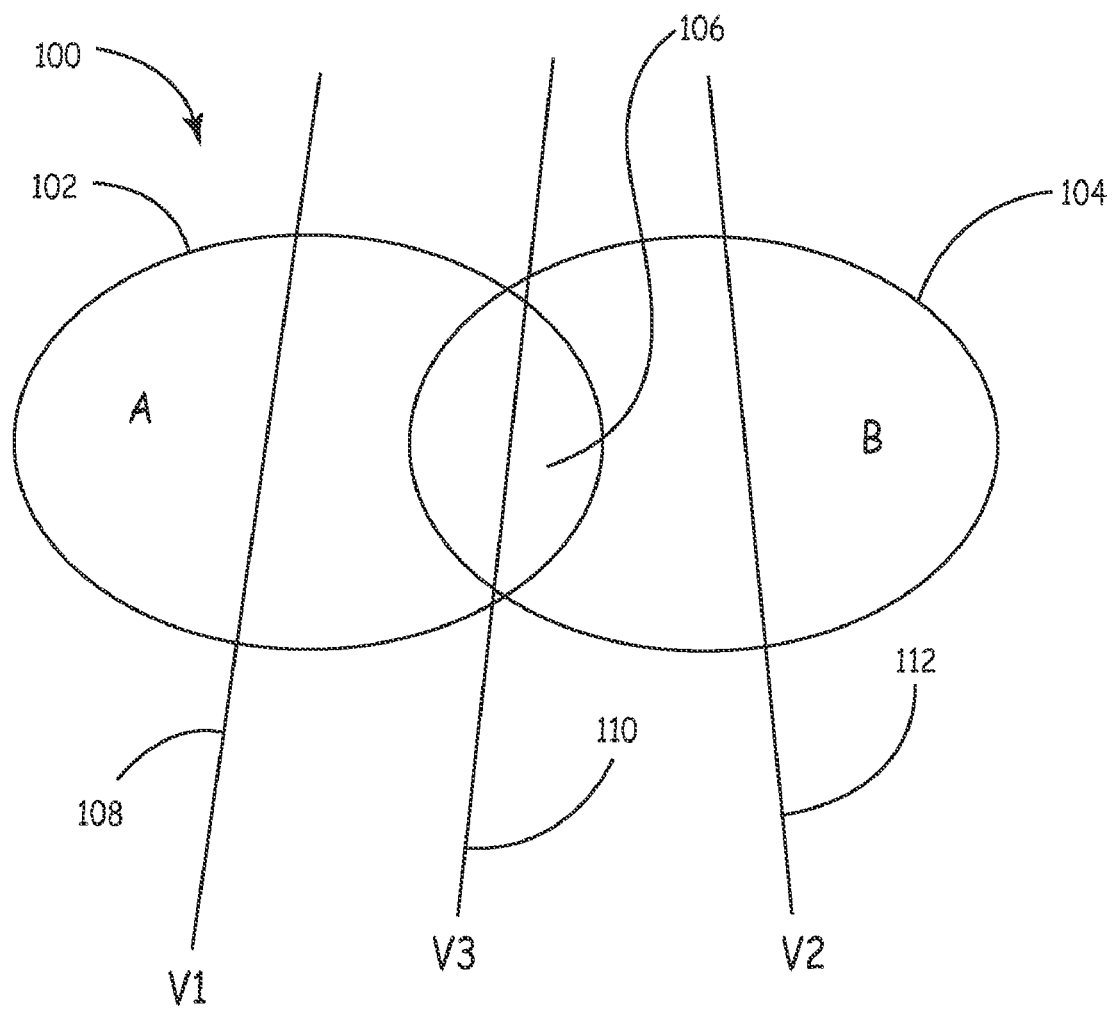
FIG. 1 is a schematic diagram of impedance vectors crossing two physiological impedance change factors.

FIG. 1 is a schematic diagram of impedance vectors crossing physiological impedance change factors. As illustrated in FIG. 1, an abstract diagram 100 illustrating a simplified example of the present invention includes one physiological factor contributing to changes in impedance over time as sensed across various vectors, Factor A, and another physiological factor contributing to changes in impedance over time as sensed across various vectors, Factor B. Impedance change contributing Factor A is represented at 102 and impedance change contributing Factor B is indicated at 104. A region of overlap 106 is formed that includes contributing Factor A and contributing Factor B. Three vectors, Vector 1 at 108, Vector 2 at 112, and Vector 3 at 110, are also illustrated. Vector 1 conceptually passes through a large portion of Factor A, while being little influenced by Factor B. Vector 2 passes through a large portion of Factor B, being little influenced by Factor A. Vector 3 passes through portions of both Factor A and Factor B and is thus influenced somewhat by both Factor A and Factor B. As a result, the sensitivity or susceptibility of Vector 1 to Factor A is high, and the sensitivity or susceptibility of Vector 1 to Factor B is low. The sensitivity of Vector 2 to Factor A is low and the sensitivity of Vector 2 to Factor B is high. The sensitivity of Vector 3 to Factor A is medium, as is the sensitivity of Vector 3 to Factor B.

Generally, the change in impedance over time across a Vector X in the simplified system of FIG. 1 is given in Equation 1 below.

$$\Delta Z_{VX} = \alpha_{VXA} * Q_A + \alpha_{VXB} * Q_B \tag{1}$$

The term $\alpha_{VXA}$ in Equation 1 is the sensitivity to impedance changes over time across Vector X caused by resistivity changes over time in Factor A. Similarly, $\alpha_{VXB}$ is used to indicate the changes over time across Vector X caused by resistivity changes over time in Factor B. $Q_A$ indicates the relative change in resistivity over time in Factor A and $Q_B$ indicates the relative change in resistivity over time in Factor B.

Equation 2 below gives the changes in impedance over time across another vector, Vector Y.

$$\Delta Z_{VY} = \alpha_{VYA} * Q_A + \alpha_{VYB} * Q_B \tag{2}$$

Equation 2 states that the changes in impedance over time across Vector Y are equal to the sensitivity to changes over time across Vector Y caused by resistivity changes over time in Factor A times the fractional resistivity changes over time in Factor A plus the sensitivity to changes over time across Vector Y caused by resistivity changes in Factor B over time times the fractional change in resistivity over time in Factor B.

$$Q_A = \Delta \rho_A / \rho_A = (\rho_{AT2} - \rho_{AT1}) / \rho_{AT1} \tag{3}$$

Equation 3 indicates that the fractional change (relative change or percentage change) in resistivity of Factor A is equal to the change in the resistivity of Factor A relative to the resistivity of Factor A. This may also be stated as indicated in Equation 3, as being the change in resistivity from Time 1 to Time 2 divided by the resistivity at Time 1.

Taken together, Equations 1 and 2 provide a system of equations that can be solved. These equations can be easily solved, even in the presence of additional factors, if the sensitivity coefficients, the α values, are not randomly occurring but have advantageous patterns. In particular, where there are multiple vectors available to select from, it will be advantageous to select Vectors X and Y such that the sensitivity values $\alpha_{VX}$ and $\alpha_{VY}$ differ only for one factor. To find or evaluate $Q_A$ in Equations 1 and 2, it is advantageous to find two vectors, X and Y, such that $\alpha_{VXA}$ is substantially different than $\alpha_{VYA}$ and such that $\alpha_{VXB}$ is substantially equal to $\alpha_{VYB}$. It may be more generally stated, that in order to solve for relative changes in Factor A over time, the sensitivity to changes in Factor A across Vectors X and Y should differ from each other, while the sensitivities across Vectors X and Y should be substantially equal for any remaining factors in which the change in impedance over time is not known and for which the contribution is significant.

Referring again to FIG. 1, in order to evaluate $Q_A$ (the relative change in resistivity in Factor A), Vectors 1 and 3 may be selected. Substituting Vectors 1 and 3 into Equations 1 and 2 results in Equations 4 and 5 below.

$$\Delta Z_{V1} = \alpha_{V1A} * Q_A + \alpha_{V1B} * Q_B \tag{4}$$

$$\Delta Z_{V3} = \alpha_{V3A} * Q_A + \alpha_{V3B} * Q_B \tag{5}$$

Equation 6 below results from subtracting equation 5 from equation 4.

$$\Delta Z_{V1} - \Delta Z_{V3} = (\alpha_{V1A} - \alpha_{V3A}) * Q_A + (\alpha_{V1B} - \alpha_{V3B}) * Q_B \tag{6}$$

Solving for $Q_A$ we arrive at Equation 7 below.

$$Q_A = (\Delta Z_{V1} - \Delta Z_{V3}) / (\alpha_{V1A} - \alpha_{V3A}) \tag{7}$$

As previously discussed, $\alpha_{V1B}$ and $\alpha_{V3B}$ are substantially equal to each other, and therefore are either zero or a very small value and may thus be ignored. In systems where the number of equations equals the number of unknowns, it is possible to use standard matrix algebra to solve for $Q_A$ and $Q_B$. As is discussed later, there may not always be a number of equations equal to the number of unknowns, but the factor changes in resistivity may still be evaluated due to similarities and differences in values of the susceptibility coefficients. Equation 7 thus indicates that given the susceptibility values, and given the measured impedance changes over time for Vector 1 and Vector 3, the resistivity changes over time in Factor A can be evaluated. As will be discussed later, the resistivity changes over time for a single factor may be highly physiologically significant, and can serve as an indicator of the progress of specific medical conditions.

The system of equations above can be further extended to include other factors.

$$\Delta Z_{VX} = \alpha_{VXA} * Q_A + \alpha_{VXB} * Q_B + \alpha_{VXC} * Q_C \tag{8}$$

$$\Delta Z_{VY} = \alpha_{VYA} * Q_A + \alpha_{VYB} * Q_B + \alpha_{VYC} * Q_C \tag{9}$$

$$\Delta Z_{VZ} = \alpha_{VZA} * Q_A + \alpha_{VZB} * Q_B + \alpha_{VZC} * Q_C \tag{10}$$

Equations 8, 9 and 10 above include a new factor, Factor C. A new vector, Vector Z, is also included. It may be noted that while equation 8 is shown for completeness, it is not needed to solve for $Q_B$ if $Q_A$ is known and $\alpha_{VXC}$ is substantially equal to $\alpha_{VYC}$. To solve for $Q_B$, since $Q_A$ is known, we can select vectors such that the sensitivity varies between the selected vectors only for Factor B, and not Factor C, with Factor A being taken care of already by the known value of $Q_A$. Selecting Vectors Y and Z leads to Equation 11 below.

$$\Delta Z_{VY} - \Delta Z_{VZ} = (\alpha_{VYA} - \alpha_{VZA}) * Q_A + (\alpha_{VYB} - \alpha_{VZB}) * Q_B + (\alpha_{VYC} - \alpha_{VZC}) * Q_C \tag{11}$$

Solving for $Q_B$ leads to Equation 12 below.

$$Q_B = ((\Delta Z_{VY} - \Delta Z_{VX}) - (\alpha_{VYC} - \alpha_{VZC}) * Q_C - (\alpha_{VYA} - \alpha_{VZA}) * Q_A) / (\alpha_{VYB} - \alpha_{VZB}) \tag{12}$$

As $\alpha_{VYC}$ and $\alpha_{VZC}$ were selected to be substantially equal to each other, the difference of these two terms is very small relative to $\alpha_{VYB} - \alpha_{VZB}$ or zero and drops out of the above equation. Therefore, $Q_B$ is solved. It should be noted that Factor C in the above equation could be a grouped or lumped factor. This can prove useful where the grouped or lumped factor is an indicator as a grouped or lumped factor of a significant medical condition.

Figure 2:
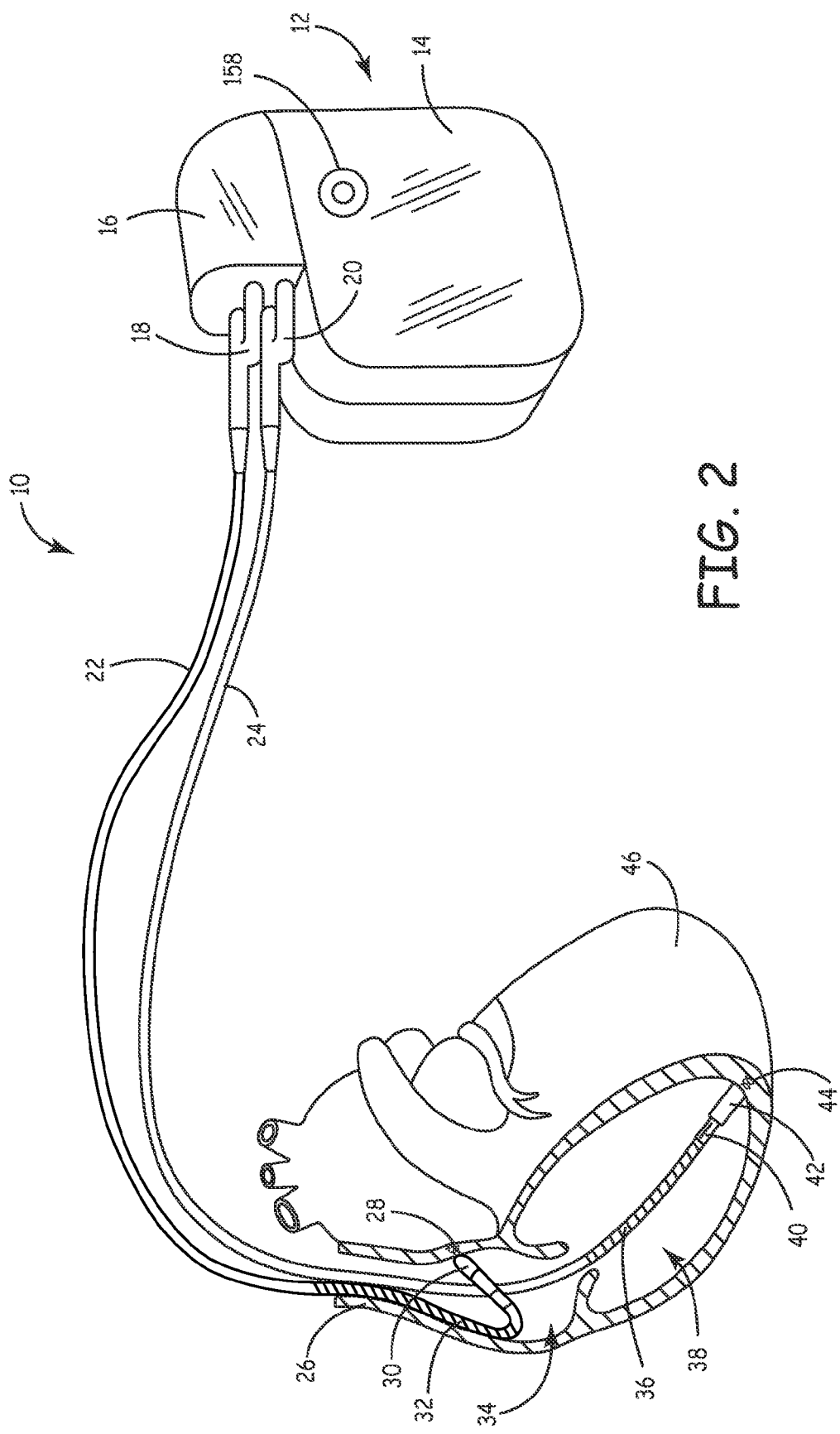
FIG. 2 is a schematic diagram of an exemplary implanted medical device system for measuring impedance changes across and/or near a heart according to the present invention.

FIG. 2 is a schematic diagram of an exemplary implanted medical device system for measuring impedance changes across and/or near a heart according to the present invention.

As illustrated in FIG. 2, an implantable medical device system 10 includes an implantable cardiac defibrillator (ICD) 12 having a housing or can 14 and a connector block 16. IMD system 10 may be implemented using any of a number of medical devices or alternative device configurations, including, but not limited to ICD 12. Other techniques or therapies responsive to electrocardiogram (EGM) signals or other patient diagnostic data, such as therapies that administer drugs in response to atrial arrhythmia, also may implement various embodiments of the invention.

IMD system 10 includes a ventricular lead, which includes an elongated insulated lead body 24, carrying three concentric coiled conductors separated from one another by tubular insulative sheaths. The distal end of the ventricular lead is deployed in right ventricle 38. Located adjacent the distal end of the ventricular lead are a ring electrode 40, an extendable helix electrode 44, mounted retractably within an insulative electrode head 42, and an elongated (approximately 5 cm) defibrillation coil electrode 36. Defibrillation electrode 36 may be fabricated from many materials, such as platinum or platinum alloy. Each of the electrodes is coupled to one of the coiled conductors within lead body 24.

Electrodes 40 and 44 are employed for cardiac pacing and for sensing ventricular depolarizations. Accordingly, electrodes 40 and 44 serve as sensors for a ventricular electrocardiogram (V-EGM). At the proximal end of the ventricular lead is a bifurcated connector 20 that carries three electrical connectors, each coupled to one of the coiled conductors.

The right ventricular (RV) lead includes an elongated insulated lead body 22, carrying three concentric coiled conductors, separated from one another by tubular insulative sheaths, corresponding to the structure of the ventricular lead. The distal end of the RV lead is deployed in right atrium 34. Located adjacent the distal end of the RV lead are a ring electrode 32 and an extendable helix electrode 28, mounted retractably within an insulative electrode head 30. Each of the electrodes is coupled to one of the coiled conductors within lead body 22. Electrodes 28 and 32 are employed for atrial pacing and for sensing atrial depolarizations. Accordingly, electrodes 28 and 32 serve as sensors for an atrial electrocardiogram (AEGM).

An elongated coil electrode 26 is provided proximal to electrode 32 and coupled to the third conductor within lead body 22. Electrode 26 is preferably at least 10 cm long and is configured to extend from the SVC toward the tricuspid valve. At the proximal end of the lead is a bifurcated connector 18 that carries three electrical connectors, each coupled to one of the coiled conductors.

Implantable ICD 12 is shown in combination with the leads, with lead connector assemblies 18 and 20 inserted into connector block 16. Outward facing portion of housing or can 14 of ICD 12 may be left uninsulated so that the uninsulated portion of the housing or can 14 optionally serves as a subcutaneous defibrillation electrode, used to defibrillate either the atria or ventricles. In addition, a button electrode 158 may also be included along housing 14.

Figure 3:
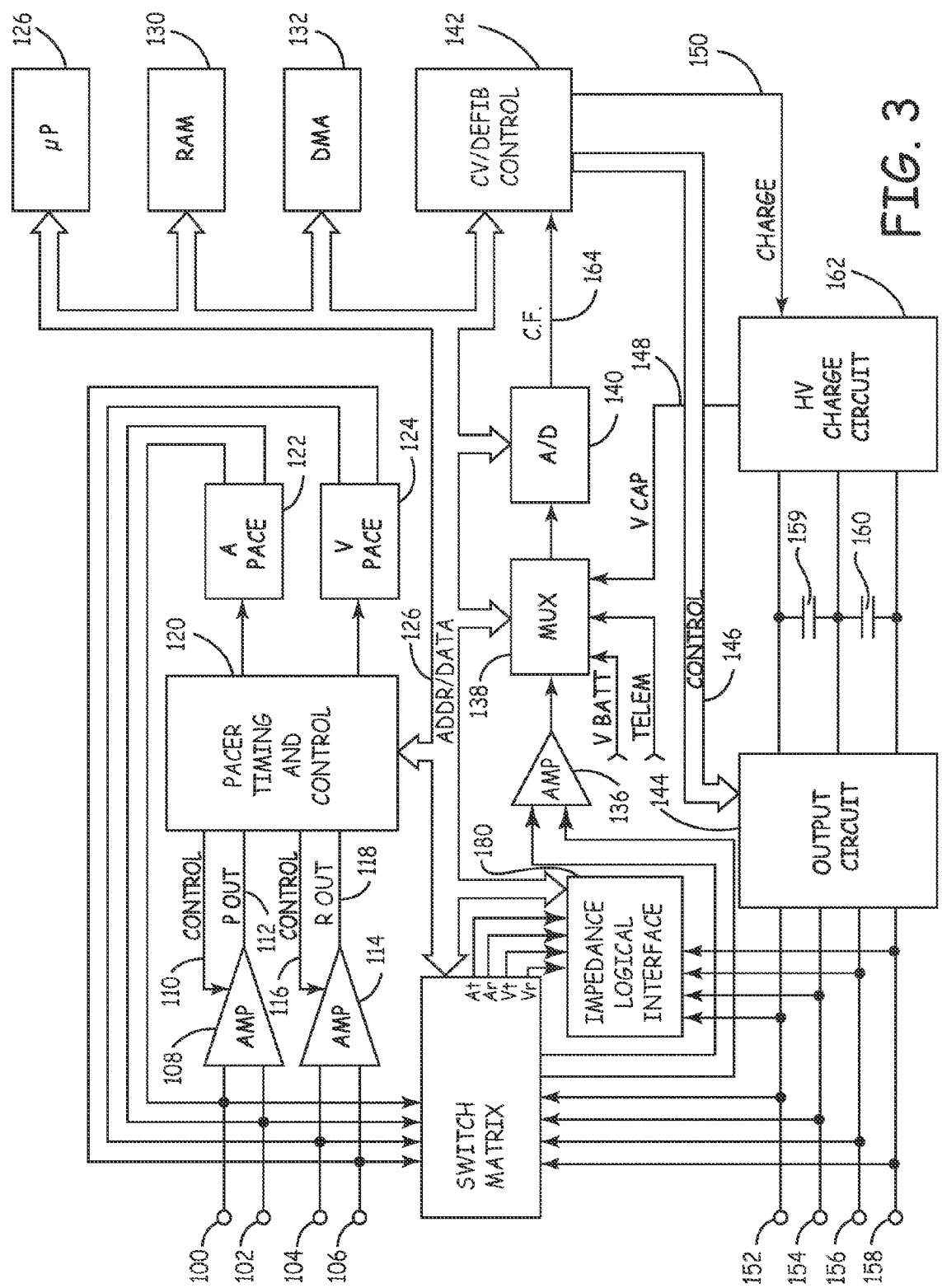
FIG. 3 is a functional schematic diagram of an implantable medical device in which the present invention may be practiced.

FIG. 3 is a functional schematic diagram of an implantable medical device in which the present invention may be practiced. FIG. 3 should be construed as an illustrative example of one type of device in which the invention may be embodied. The invention is not limited to the particular type of device shown in FIG. 3, but may be practiced in a wide variety of device implementations, such as a pacemaker or an ICD. In addition, the invention is not limited to the implementation shown in FIG. 3. For example, the invention may be practiced in a system that includes more or fewer features than are depicted in FIG. 3.

The device illustrated in FIG. 3 is provided with an electrode system including electrodes. For clarity of analysis, the pacing/sensing electrodes 100, 102, 104, and 106 are shown as logically separate from pacing/defibrillation electrodes 152, 154, 156 and 158. Electrodes 152, 154, 156 and 158 correspond respectively to an atrial defibrillation electrode, a ventricular defibrillation electrode, the uninsulated portion of the housing of the implantable PCD and a button electrode positioned along the housing. Electrodes 152, 154, 156 and 158 are coupled to a high voltage output circuit 144. High voltage output circuit 144 includes high voltage switches controlled by cardioversion/defibrillation (CV/defib) control logic 142 via a control bus 146. The switches within output circuit 144 control which electrodes are employed and which are coupled to the positive and negative terminals of a capacitor bank including capacitors 159 and 160 during delivery of defibrillation pulses.

Electrodes 104 and 106 are located proximate a ventricle and are coupled to an R-wave sense amplifier 114. Operation of amplifier 114 is controlled by pacing circuitry 120 via control lines 116. Amplifier 114 may perform other functions in addition to amplification, such as filtering signals sensed by electrodes 104 and 106. Amplifier 114 may also include a comparator that compares the input signal to a preselected ventricular sense threshold. Amplifier 114 outputs a signal on an R-out line 118 whenever the signal sensed between electrodes 104 and 106 exceeds the ventricular sense threshold.

Electrodes 100 and 102 are located on or in an atrium and are coupled to a P-wave sense amplifier 108. Operation of amplifier 108 is controlled by pacing circuitry 120 via control lines 110. Amplifier 108 may perform other functions in addition to amplification, such as filtering signals sensed by electrodes 100 and 102. Amplifier 108 may include a comparator that compares the input signal to a preselected atrial sense threshold, which is usually different from the ventricular sense threshold. Amplifier 108 outputs a signal on a P-out line 112 whenever the signal sensed between electrodes 100 and 102 exceeds the atrial sense threshold.

A switch matrix 134 selectively couples the available electrodes to a wide band (2.5-150 Hz) amplifier 136 for use in signal analysis. Signal analysis may be performed using analog circuitry, digital circuitry, or a combination of both.

A microprocessor 128 controls the selection of electrodes via a data/address bus 126. The selection of electrodes may be varied as desired. Amplifier 136 provides signals from the selected electrodes to a multiplexer 138, which provides the signals to an analog-to-digital (A/D) converter 140 for conversion to multi-bit digital signals and to a random access memory (RAM) 130 under control of a direct memory access (DMA) circuit 132 for storage.

The PCD illustrated in FIG. 3 also contains circuitry for providing cardiac pacing, cardioversion, and defibrillation therapies. For example, pacer timing/control circuitry 120 may include programmable digital counters that control the basic time intervals associated with DDD, VVI, DVI, VDD, AAI, DDI, and other modes of single and dual chamber pacing. Pacer timing/control circuitry 120 may also control escape intervals associated with anti-tachyarrhythmia pacing in both the atrium and the ventricle, employing any of a number of anti-tachyarrhythmia pacing therapies.

Intervals defined by pacing circuitry 120 include, but are not limited to, atrial and ventricular pacing escape intervals, refractory periods during which sensed P-waves and R-waves are ineffective to restart timing of the escape intervals, and pulse widths of the pacing pulses. Microprocessor 128 determines the durations of these intervals based on stored data in RAM 130 and communicates these durations to pacing circuitry 120 via address/data bus 126. Microprocessor 128 also determines the amplitude of pacing pulses and communicates this information to pacing circuitry 120.

During pacing, pacing timing/control circuitry 120 resets its escape interval counters upon sensing P-waves and R-waves as indicated by signals on lines 112 and 118. The escape interval counters are reset in accordance with the selected mode of pacing on time-out trigger generation of pacing pulses by pacer output circuits. These pacer output circuits include an atrial pacer output circuit 122 coupled to electrodes 100 and 102, and a ventricular pacer output circuit 124 coupled to electrodes 104 and 106. Pacing timing/control circuitry 120 also resets the escape interval counters when the pacer output circuits generate pacing pulses, thereby controlling the basic timing of cardiac pacing functions, including anti-tachyarrhythmia pacing. Microprocessor 128 determines the durations of the intervals defined by the escape interval timers and communicates these durations using data/address bus 126. The value of the count present in the escape interval counters when reset by sensed R-waves and P-waves may be used to measure the durations of R-R intervals, P-P intervals, P-R intervals, and R-P intervals. These measurements are stored in RAM 130 and used to detect tachyarrhythmias.

Microprocessor 128 typically operates as an interrupt-driven device under control of a program stored in an associated read only memory (ROM, not shown) and is responsive to interrupts from pacer timing/control circuitry 120 corresponding to the occurrence of sensed P-waves and R-waves and to the generation of cardiac pacing pulses. Data/address bus 126 provides these interrupts. In response to these interrupts, microprocessor 128 performs any necessary mathematical calculations, and pacer timing/control circuitry 120 may update the values or intervals that it controls.

When an anti-tachyarrhythmia pacing regimen is indicated based on a detected atrial or ventricular tachyarrhythmia, appropriate timing intervals are loaded from microprocessor 128 into pacer timing/control circuitry 120. In the event that generation of a cardioversion or defibrillation pulse is required, microprocessor 128 employs an escape interval counter to control timing of such cardioversion and defibrillation pulses, as well as associated refractory periods.

In response to the detection of atrial, ventricular fibrillation or tachyarrhythmia requiring a cardioversion pulse, microprocessor 128 activates cardioversion/defibrillation control circuitry 142, which uses high voltage charging control lines 150 to cause a charging circuit 162 to initiate charging of high voltage capacitors 158 and 160. A VCAP line 148 monitors the voltage on high voltage capacitors 158 and 160 and communicates this information through multiplexer 138. When this voltage reaches a predetermined value set by microprocessor 128, A/D converter 140 generates a control signal on Cap Full (CF) line 164 to terminate charging. Thereafter, pacer timing/control circuitry 120 controls timing of the delivery of the defibrillation or cardioversion pulse. Following delivery of the fibrillation or tachyarrhythmia therapy, microprocessor 128 returns the device to cardiac pacing and waits for a subsequent interrupt due to pacing or the occurrence of a sensed atrial or ventricular depolarization.

An output circuit 144 delivers the cardioversion or defibrillation pulses as directed by control circuitry 142 via control bus 146. Output circuit 144 determines whether a monophasic or biphasic pulse is delivered, the polarity of the electrodes, and which electrodes are involved in delivery of the pulse. Output circuit 144 may include high voltage switches that control whether electrodes are coupled together during delivery of the pulse. Alternatively, electrodes intended to be coupled together during the pulse may simply be permanently coupled to one another, either inside or outside the device housing. Similarly, polarity may be preset in some implantable defibrillators.

An impedance measurement logical interface (LIMLI) 180 is provided and employed when initiated by microprocessor 128 on address/data bus 126 either automatically on a periodic basis or in response to a programmed command received through telemetry. According to the present invention, impedance is measured along selected vectors extending through the tissue of the body using various electrodes, as will be described below in detail.

One embodiment of the invention utilizes a pacing device, having firmware adapted to stimulate tissue at sub-threshold levels and to sense various impedance values across various vectors using various electrodes coupled to the device. Presently available implanted cardiac devices have impedance sensing capability that is used to measure minute ventilation and physiological activity. Circuitry and systems suitable for stimulating cardiac tissue and measuring impedance across the tissue is described, for example, in U.S. Pat. No. 5,562,711 (Yerich et al.), herein incorporated by reference. Other impedance measuring circuitry is disclosed in U.S. Pat. No. 6,070,100 (Bakels et al.), herein incorporated by reference.

It is to be understood that the impedance measurements include "raw" measurements and "processed" measurements. Processed measurements include "average" measurements formed of the averages of more than one measurement, "filtered" measurements formed of filtered impedance measurements, "derivative" impedance measurements formed of the first or higher order derivatives of impedance measurements, "selected" impedance measurements formed of the highest or lowest impedance measurements from a set of impedance measurements, "gated" impedance measurements taken from peaks or troughs in or gated to respiratory or cardiac cycles, and "inverted" impedance measurements formed of inverted impedance measurements. The selected impedance measurements can be used to catch an impedance minimum or maximum from a time region including a small number, for example, 1 to 10, of impedance measurements. In embodiments having more than one pair of sensing electrodes, two or more sensing electrode impedance measurements can be added together to form an "augmented" impedance measurement. Similarly, one or more sensing electrode measurement can be subtracted from one or more other sensing electrode measurement to form a "subtracted" impedance measurement. Both the augmented and subtracted impedance measurements can provide valuable information gathered from the similarities or differences encountered by the stimulating current's path to the sensing electrodes. Unless noted otherwise, the impedance measurements used in all methods according to the present invention can be any of the aforementioned raw and processed impedance measurements and combinations thereof.

It also is to be understood that the system depicted here need not be limited to these lead positions, electrode sizes, and numbers of electrodes. Other embodiments of this system include multi-polar electrodes (3 or more electrodes on a single lead), defibrillation coils, and/or the pacemaker can and/or button electrodes on the can. In some embodiments, the impedance measurement can be made between two or more stimulating electrodes and two or more sensing electrodes. which are not necessarily exclusive of each other. Specifically, some of the stimulating electrodes may also be sensing electrodes.

Various paths or vectors may be drawn between any combination of electrodes connected to implanted device can 14 or connected to leads 22 and 24. One electrode may serve as an emitter while another electrode may serve as a collector, with yet another pair of electrodes used to measure the electrical potential between those electrodes, to determine the impedance across the paths or vectors. The emitter and collector can share one or both electrodes with the electrode pair used to sense the voltage, in bipolar and tripolar configurations, respectively. In quadrapolar configurations, the emitter, collector, and measuring electrode pair are distinct electrodes. The term "vector" and "path" may be used interchangeably for the purposes of the present application.

For example, a first vector used to measure impedance changes, Vector 1, is formed by a stimulation path and a sense path between RV coil 36 and can 14. Vector 1 is a bi-polar vector, utilizing RV coil 36 as the emitter and can 14 as the collector, and measuring voltage at RV coil 36 and can 14. Impedance changes may also be measured across another vector, Vector 2, formed by a stimulation path from RV ring electrode (Vr) 40 to can 14 and a sense path from RV coil 36 to can 14. Vector 2 is a tri-polar vector, utilizing RV ring 40 as the emitter and can 14 as the collector, and using RV coil 36 and can 14 as voltage measuring points.

Impedance changes may also be measured across a vector, Vector 3, formed by a stimulation path and a sense path from RV ring electrode 40 to can 14. Vector 3 is a ventricular bi-polar vector, utilizing right ventricular ring electrode 40 as the emitter and can 14 as the collector, and also using right ventricular ring electrode 40 and can 14 as voltage measuring electrodes. Impedance changes may also be measured across another vector, Vector 4, formed by a stimulation path from RV ring electrode 40 to can 14 and a sense path from RV tip electrode (Vt) 44 to can 14. Vector 4 is a ventricular tri-polar vector, utilizing right ventricular ring electrode 40 as the emitter and can 14 as the collector, and also using right ventricular tip electrode 44 and can 14 as voltage measuring electrodes. Another vector may be used, Vector 5, formed by a stimulation path from RV coil electrode 40 to can 14 and a sense path from RV coil electrode 40 to button 158. Vector 5 is a tri-polar vector, using right ventricular coil 40 as the emitter and can 14 as the collector, and utilizing right ventricular coil 40 and button 158 on the can 14 as voltage measuring electrodes.

The above described vectors are but a few of the possible leads, electrodes, and vectors that can be used according to the present invention. Other electrodes that can be used include superior vena cava coils, right atrial ring electrodes, right atrial tip electrodes, left atrial coils, left atrial ring electrodes, left atrial tip electrodes, left ventricular ring electrodes, left ventricular tip electrodes, including leads place via the coronary sinus, along with electrodes placed endocardially or epicardially. Several impedance measuring electrodes and vectors that can be used to advantage in the present invention are discussed in U.S. Published Patent Application No. 2002/0002389, herein incorporated by reference. More combinations can be visually created by inspection and are well known to the inventor and will become apparent to those skilled in the art. Additional combinations can be created using additional electrodes not limited to those shown in the Figures.

Vector 6 is an AV quadra-polar vector, utilizing right ventricular ring electrode 40 as an emitter and right atrial ring electrode 32 as a collector, and using a right ventricular tip 44 and right atrial tip 28 as the voltage measuring electrodes. Vector 7 is a brady, tri-polar vector utilizing right atrial ring electrode 32 as the emitter and the can 14 as a collector, and utilizing right atrial tip 28 and can 14 as voltage measuring electrodes.

FIG. 4 illustrates a table or susceptibility matrix for the various vectors previously described, along with two others, not requiring separate illustration and well known to those skilled in the art. FIG. 4 includes the sensitivities or susceptibilities of the various vectors to the various physiological impedance factors, as will be discussed further. The various factors included in FIG. 4 are lung resistivity, blood resistivity, heart muscle resistivity, skeletal muscle resistivity, heart volume, and lung volume. Vectors 1 through 7 are as previously described. The column labeled "Vector" in FIG. 4 includes the stimulation electrode pair/sense electrode pair. Vector 2 thus refers to stimulation between the right ventricular ring and can, and sensing between the right ventricular coil and can. Inspection of FIG. 4 shows, for example, that Vector 3 is extremely sensitive to changes in blood resistivity relative to the other various physiological factors. Vector 2 may be seen to be much less sensitive to changes in blood resistivity than Vector 3. It may also be seen that Vectors 1 and 2 vary significantly in the sensitivity to blood resistivity, while having very similar sensitivities to the remaining factors. The sensitivities or susceptibilities for Vectors 1 through 4 and 6 through 7 have been theoretically derived from mathematical modeling, and validated. The sensitivities or susceptibilities can be further refined and calibrated through testing by those skilled in the art, using the teachings of the present invention. Vector 5 contains values in FIG. 4 that have been estimated based on physical physiological considerations and the other values in the table.

Equation 13 below gives the change in impedance over time for a selected vector as a function of the sensitivities or susceptibilities of a factor in FIG. 4. There may be other factors for which there are substantial impedance contributions but for which there are no substantial impedance change contributions. One such example is the distance between two electrodes for which the distance is expected to remain fixed. As used in the present application, the impedance contributions refer to impedance contributions for which changes can be expected over time.

$$\Delta Z = \alpha_L * Q_L + \alpha_B * Q_B + \alpha_{HM} * Q_{HM} + \alpha_{SM} * Q_{SM} + \alpha_{HV} * K_{HV} + \alpha_{LV} * K_{LV} \tag{13}$$

Q is equal to $\Delta\rho/\rho$, and K is equal to $\Delta V/V$. L represents lung resistivity, B represents blood resistivity, HM represents heart muscle resistivity, SM represents skeletal muscle resistivity, HV represents heart volume, and LV represents lung volume. As will be discussed below, in some methods, the lung resistivity and heart volume resistivity, L and HV may be lumped together as a single parameter as an indicator of heart failure, as is the case with fluid overload in congestive heart failure.

Using the values of the table in FIG. 4 together with equation 13, and the various methods previously described for the general statement of the invention, we may now derive physiologically meaningful changes in factors.

The changes in blood resistivity are often of interest to a treating physician. Changes in blood resistivity can indicate electrolyte imbalances and also the effectiveness of blood thinners or other prescribed medications. Inspection of FIG. 4 shows that Vectors 1 and 2 differ in the sensitivity to changes in blood resistivity but have substantially the same sensitivities as between the two vectors to the other factors in FIG. 4. This indicates that Vectors 1 and 2 may be evaluated to solve for the fractional change in blood resistivity. Inserting the values for Vector 1 into equation 13 and the values for Vector 2 into equation 13 allows us to solve for $Q_B$. The impedance can be measured across Vector 1 at time 1 and the impedance measured across Vector 2 also at time 1, or a very short time after time 1, for example, microseconds after time 1. At a later time, for example, hours, days or weeks later, the impedance across Vectors 1 and 2 may be evaluated at time 2. The change in impedance over time for Vector 2 may be subtracted from the change in impedance over time for Vector 1, leading us to the result of equation 14 below.

$$\Delta Z_{V1} - \Delta Z_{V2} = 0 * Q_L + (0.13 - 0.023) * Q_B - 0.01 * Q_{HM} + 0 * Q_{SM} - 0 * K_{HV} + 0.002 * K_{LV} \quad (14)$$

The contribution difference by $Q_{HM}$ is small and may be neglected, as may be the contribution difference by $K_{LV}$. Solving for $Q_B$, $Q_B = (\Delta Z_{V1} - \Delta Z_{V2})/0.107$. $Q_B$ has thus been determined using equation 13, the susceptibility matrix table, and the measurements from Vectors 1 and 2. The mathematics involved in determining $Q_B$ can be implemented in several ways. In some methods, the impedance changes over time are periodically measured by the implanted medical device and stored. The stored values can be retrieved periodically or on demand by a telemetry device. The telemetry device itself, or a separate computing device, or the implanted device itself, can implement the above-described methods in order to determine the change in blood resistivity over time. This change in blood resistivity, or any other factor according to the present invention, may be plotted, analyzed, and transmitted to a treating physician for further analysis. A significant change in the blood resistivity, or any other factor in the present invention, may be flagged or indicated as deserving particular attention. Some methods alert the patient and/or a treating physician via a patient alert system, which can include a computer network, including the Internet and Websites, in either or both directions between patient and physician.

The relative change in heart muscle resistivity is also of interest. The resistivity of the heart muscle can change as a function of the degree of perfusion of the heart muscle. A decrease in perfusion, for example, caused by a decrease in blood being supplied by the coronary arteries, can be indicative of significant blockage or of myocardial infarction. The change in the heart muscle relative resistivity is thus a factor of particular interest. Inspection of FIG. 4 shows that Vectors 2 and 3 differ in their sensitivity to changes in heart muscle resistivity, while remaining approximately the same for other substantially contributing factors. Vectors 2 and 3 do differ in their sensitivity to blood resistivity, but the change in blood resistivity, $Q_B$, has previously been solved. The values from FIG. 4 for Vector 2 and Vector 3 may be substituted into Equation 13. Equation 13 evaluated at Vector 2 may then be subtracted from the values for Equation 13 for Vector 3, resulting in Equation 15.

$$\Delta Z_{V3} - \Delta Z_{V2} = 0.020 * Q_L + 1.257 * Q_B + 0.44 * Q_{HM} + 0.04 * Q_{SM} + 0.0003 * K_{HV} + 0.003 * K_{LV} \quad (15)$$

The value for $Q_B$ is already known. The contributions for $Q_L$, $Q_{SM}$, $K_{HV}$, and $K_{LV}$ are significantly less than those of $Q_B$ and $Q_{HM}$, and may therefore be initially treated as 0. Using the previously obtained value for $Q_B$, Equation 16 results, solving for $Q_{HM}$.

$$Q_{HM} = ((\Delta Z_{V3} - \Delta Z_{V2}) - 1.257 * Q_B)/0.44 \quad (16)$$

$Q_{HM}$ has thus been solved for, providing an indication of heart muscle perfusion. As discussed with respect to other factors, the relative or fractional changes in $Q_{HM}$ can be determined by measuring the changes in impedance over time across Vectors 2 and 3, with the changes in $Q_{HM}$ automatically computed and analyzed.

The changes in skeletal muscle resistivity, $Q_{SM}$, are also of interest. A significant change in the skeletal muscle resistivity can be indicative of inflammation or edema of muscle surrounding the pocket containing the implanted medical device. A change in $Q_{SM}$ can be indicative by hematoma, bleeding in the pocket. A significant change in $Q_{SM}$ can also be indicative of infection in the pocket.

Inspection of FIG. 4 shows that Vector 5 has a significant difference in sensitivity for skeletal muscle relative to the other vectors. Vector 5, as previously discussed, is an estimate of the expected values for the sensitivities. It may be noted that the values for the blood resistivity and heart muscle resistivity may not be of importance as to their exact values as the values for $Q_B$ and $Q_{HM}$ are already known. What is significant is that the changes in sensitivity for skeletal muscle of Vector 5 relative to the other vectors is a significantly large difference. Using the methods previously described, $Q_{SM}$ may be solved for by evaluating Equation 13 for Vector 5 and another vector, for example, Vector 1. When the differences in Equation 13 for Vectors 1 and 5 are evaluated, with the values for $Q_B$ and $Q_{HM}$ already being known, and the sensitivity differences in lung resistivity, heart volume, and lung volume being extremely small, $Q_{SM}$ can be solved for. Given the values in FIG. 4, another method solves for $Q_{SM}$ using Vectors 1 and 5 without requiring knowledge of any other factors. Evaluating the change in $Q_{SM}$ thus provides an indication of hematoma or infection in the pocket, which can be indicated as a change of interest to the treating physician.

The value for $K_{LV}$, the fractional change in lung volume, may also be evaluated using equations according to the present invention and the proper sensitivity coefficients. Inspection of FIG. 4 indicates a small change in sensitivities or a difference in sensitivities between Vectors 1 and 2. These differences in sensitivities are small, relative to the differences previously encountered for the other factors. This small difference in sensitivities means that the resulting value may be effected by noise and uncertainty in the values. The accuracy of the resulting $K_{LV}$ value will thus likely be less accurate using only the sensitivity values found in FIG. 4. Nonetheless, $K_{LV}$ can be solved for by substituting the values for Vector 1 and Vector 2 into Equation 13 and subtracting the values for Vector 1 from the values for Vector 2. The values for the sensitivity of heart volume are equal to each other as between Vectors 1 and 2, thus removing heart volume as a factor in the equation. The resulting $K_{LV}$ can give an indication in changes over time for the average lung volume. $Q_B$, $Q_{HM}$ and $Q_{SM}$ have been previously solved, and $K_{LV}$ can be determined, and tracked, with the changes noted and reported over time.

The changes in lung resistivity and heart volume, $Q_L$ and $K_{LV}$, are of interest as a group, as they are indicative of heart failure. With Equation 13 thus solved for all factors but lung resistivity and heart volume change, a change in impedance over time may thus have the blood resistivity, heart muscle resistivity, skeletal muscle resistivity, and lung volume change accounted for, leaving only the lung resistivity and heart volume change on one side of the equation. The combined lung resistivity and heart volume change may thus be tracked as well, as a group. The changes in the combined lung resistivity and heart volume change may also be tracked over time, with significant changes noted, reported, and further analyzed by a treating physician. This combined change can be of particular value in tracking congestive heart failure.

Figure 5:
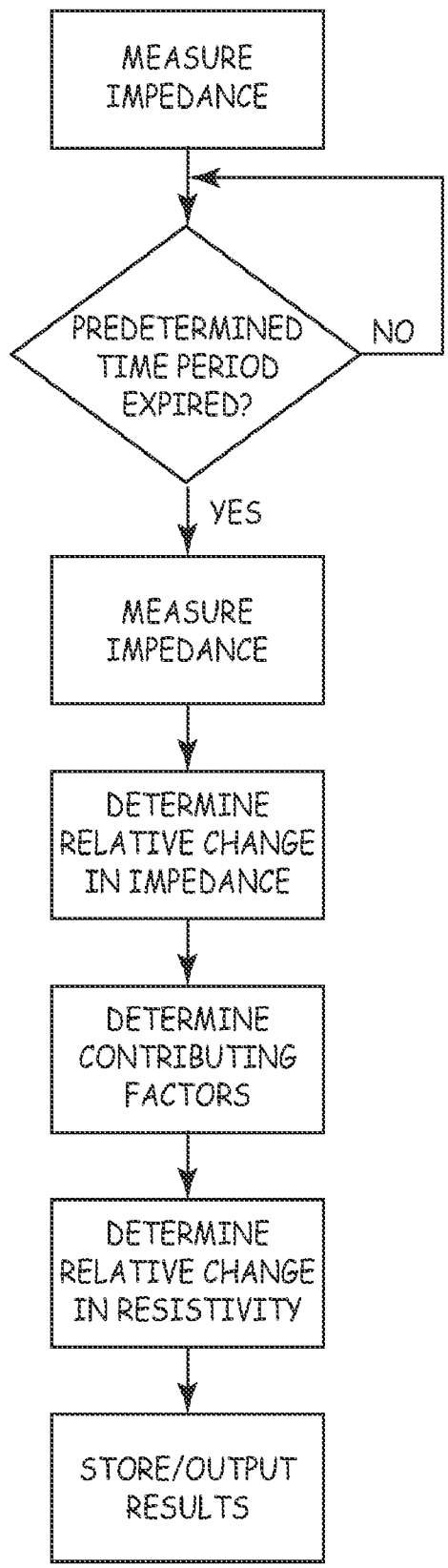
FIG. 5 is a flowchart illustrating a method for isolating impedance changes over time to physiological factors according to the present invention.

FIG. 5 is a flowchart illustrating a method for isolating impedance changes over time to monitor physiological factors according to the present invention. According to the present invention, an implantable medical device utilizing the method for identifying cardiac insult of the present invention can be programmed to determined changes in all or any number of the factors listed in the table of FIG. 4. For example, as illustrated in FIG. 5, a method for monitoring a plurality of physiological factors contributing to physiological conditions of a patient, according to the present invention includes measuring impedance along any number of the vectors in the table of FIG. 4, Step 200, waiting a predetermined time period, such as hours, days, weeks, Step 202, and measuring the impedance along the vectors again, Step 204. Based on the two measured impedances along the predetermined vectors, a relative change in impedance is determined, Step 206. Using the table of FIG. 4, the desired programmed physiological factors of the physiological factors included, such as lung resistivity, blood resistivity, heart muscle resistivity, skeletal muscle resistivity, heart volume and lung volume, are identified, and minimally contributing factors are determined for the programmed physiological factors, Step 208. Relative change in resistivity for the programmed physiological factors is then determined, Step 210, and the results are stored, or output to an external device, such as a programmer, a network, a data transmission bus, or a patient alert device, Step 212.

For example, if the desired programmed physiological factor is blood resistivity, impedance is measured along vectors 1 and 2 of the Table in FIG. 4, and the minimally contributing factors are determined to be lung resistivity, heart muscle resistivity, skeletal muscle resistivity, heart volume and lung volume. The relative change in resistivity for this physiological factor is then determined using the equation for obtaining blood resistivity $Q_B=(\Delta Z_{V1}-\Delta Z_{V2})/0.107$ obtained from equation 13 as described above, with $\Delta Z_{V1}-\Delta Z_{V2}$ being equal to the relative change determined in Step 206.

If the desired physiological factor is heart muscle resistivity, impedance is measured along vectors 1, 2 and 3 of the Table in FIG. 4, and the minimally contributing factors are determined to be lung resistivity, skeletal muscle resistivity, heart volume and lung volume. The relative change in resistivity is determined for blood resistivity, and the relative change in resistivity is determined for heart muscle resistivity using equation (16) as described above, with $\Delta Z_{V3}-\Delta Z_{V2}$ being equal to the relative change in impedance determined in Step 206.

In the same way, if the desired physiological factor is skeletal muscle resistivity, impedance is measured along vectors 1, 2, 3 and 5 of the Table in FIG. 4, and the minimally contributing factors are determined to be lung resistivity, heart volume and lung volume. The relative change in resistivity is determined for skeletal muscle using values determined for blood resistivity and heart muscle resistivity, using Equation 13, with the relative change in impedance determined in Step 206 being $\Delta Z_{V5}-\Delta Z_{V1}$ if vectors 1 and 5 are utilized, $\Delta Z_{V5}-\Delta Z_{V2}$ if vectors 2 and 5 are utilized (and $Q_B$ is determined using vectors 1 and 2 as described above), $\Delta Z_{V5}-\Delta Z_{V3}$ if vectors 3 and 5 are utilized (and $Q_B$ and $Q_{HM}$ are determined using vectors 1-3), $\Delta Z_{V5}-\Delta Z_{V4}$ if vectors 4 and 5 are utilized (and $Q_B$ and $Q_{HM}$ are determined using vectors 1-3). As described below, lung resistivity and heart volume are computed in the same way using Equation 13, with vectors 6 and 7 being utilized so that the relative change in impedance determined in Step 206 is $\Delta Z_{V6}-\Delta Z_{V5}$ for example, and the values for the remaining factors previously obtained are used.

The present invention may be extended by those skilled in the art from inspection of the location of various leads. In one example, a vector from a first button on the can to a second button on the can is unlikely to be sensitive to changes in lung volume. Similarly situated electrodes are likely to have similar sensitivities to the same factor, even when the sensitivities are substantial. In another example, a vector from the RV coil and SVC coil will be more sensitive to heart volume, and much less sensitive to skeletal muscle changes.

The present invention explicitly includes within its scope implantable cardiac devices executing programs or logic implementing methods according to the present invention. The present invention's scope also includes computer programs or logic capable of being executed, directly or indirectly, on implantable medical device impedance data. Computer readable media having instructions for implementing or executing methods according to the present invention are also within the scope of the present invention. Impedance factor isolating methods, devices implementing those methods, computer programs implementing those methods, and computer readable media containing programs implementing those methods are also within the scope of the invention. The computer readable medium includes any type of computer readable memory, such as floppy disks, conventional hard disks, CD-ROMS, Flash ROMS, nonvolatile ROM, and RAM.

While a particular embodiment of the present invention has been shown and described, modifications may be made. It is therefore intended in the appended claims to cover all such changes and modifications, which fall within the true spirit and scope of the invention.

The invention claimed is:

1. A method for monitoring a plurality of physiological factors contributing to physiological conditions of a patient in an implantable medical device, wherein the plurality of physiological factors are selected from the group consisting of lung resistivity, blood resistivity, heart muscle resistivity, skeletal muscle resistivity, heart volume and lung volume, and wherein one or more of the plurality of physiological factors contribute to the impedance of a vector, the method comprising:

determining a first impedance across each of a plurality of vectors;

determining a second impedance across each of the plurality of vectors subsequent to determining the first impedance;

for each of the plurality of vectors, determining a difference value between the first impedance for the vector and the second impedance for the vector;

determining, based on an identification of a first physiological factor of the plurality of physiological factors and first minimally contributing physiological factors of the plurality of physiological factors associated with the first physiological factor, a relative change in tissue resistivity corresponding to the first physiological factor based on at least some of the determined difference values and physiological factors of the plurality of physiological factors other than the first minimally contributing physiological factors; and, evaluating the relative change in tissue resistivity corresponding to the first physiological factor to determine whether the first physiological factor is an indicator of a medical condition, wherein, for each of the first minimally contributing physiological factors, a sensitivity of at least two of the plurality of vectors to the first physiological factor is substantially similar.

2. The method of claim 1, wherein the first physiological factor is blood resistivity.

3. The method of claim 1, wherein the plurality of vectors comprises a first vector and a second vector, the first vector including a first stimulation path and a first sense path extending between a first electrode, positioned within a ventricle of the heart, and an uninsulated portion of a housing of the device, and the second vector including a second stimulation path, extending between a second electrode, positioned within a ventricle of the heart, and the uninsulated portion of the housing, and a second sense path extending between the first electrode and the uninsulated portion of the housing.

4. The method of claim 3, further comprising:
based on an identification of a second physiological factor of the plurality of physiological factors and second minimally contributing physiological factors of the plurality of physiological factors associated with the second physiological factor, determining a relative change in tissue resistivity corresponding to the second physiological factor based on physiological factors of the plurality of physiological factors other than the second minimally contributing physiological factors, at least some of the difference values, and the determined relative change in tissue resistivity for first physiological factor; and
evaluating the relative change in tissue resistivity corresponding to the second physiological factor to determine whether the second physiological factor is an indicator of a medical condition,
wherein, for each of the second minimally contributing physiological factors, a sensitivity of at least two of the plurality of vectors to the second physiological factor is substantially similar.

5. The method of claim 4, wherein the first physiological factor is blood resistivity and the second physiological factor is lung volume.

6. The method of claim 3, further comprising:
based on an identification of a second physiological factor of the plurality of physiological factors and second minimally contributing physiological factors of the plurality of physiological factors associated with the second physiological factor, determining a relative change in tissue resistivity corresponding to the second physiological factor based on physiological factors of the plurality of physiological factors other than the second minimally contributing physiological factors, at least some of the difference values, and the determined relative change in tissue resistivity for the first physiological factor, wherein the plurality of vectors further includes a third vector including a third stimulation path and a third sensing path extending between the second electrode and the uninsulated portion; and
evaluating the relative change in tissue resistivity corresponding to the second physiological factor to determine whether the second physiological factor is an indicator of a medical condition,
wherein, for each of the second minimally contributing physiological factors, a sensitivity of at least two of the plurality of vectors to the second physiological factor is substantially similar.

7. The method of claim 6, wherein the first physiological factor is blood resistivity and the second physiological factor is heart muscle.

8. The method of claim 1, wherein the plurality of vectors comprises a first vector and a second vector, the first vector including a first stimulation path and a first sense path extending between a first electrode, positioned within a ventricle of the heart, and an uninsulated portion of a housing of the device, and the second vector including a second stimulation path extending between the first electrode and the uninsulated portion of the housing and a second sense path extending between the first electrode and a second electrode, positioned along the housing.

9. The method of claim 8, wherein the first physiological factor is skeletal muscle resistivity.

10. The method of claim 4, wherein the plurality of vectors further comprises a third vector including a third stimulation path extending between the first electrode and the uninsulated portion of the housing and a third sensing path extending between the first electrode and a third electrode positioned along the housing.

11. The method of claim 10, wherein the first physiological factor is blood resistivity and the second physiological factor is skeletal muscle resistivity.

12. The method of claim 6, further comprising:
based on an identification of a third physiological factor of the plurality of physiological factors and third minimally contributing physiological factors of the plurality of physiological factors associated with the third physiological factor, determining a relative change in tissue resistivity corresponding to the third physiological factor based on physiological factors of the plurality of physiological factors other than the third minimally contributing physiological factors, at least some of the difference values, and the determined relative change in tissue resistivity for the first physiological factor, wherein the plurality of vectors further includes a fourth vector including a fourth stimulation path extending between the first electrode and the uninsulated portion of the housing and a fourth sensing path extending between the first electrode and a third electrode positioned along the housing; and
evaluating the relative change in tissue resistivity corresponding to the third physiological factor to determine whether the third physiological factor is an indicator of a medical condition,
wherein, for each of the third minimally contributing physiological factors, a sensitivity of at least two of the plurality of vectors to the third physiological factor is substantially similar.

13. The method of claim 12, wherein the first physiological factor is blood resistivity, the second physiological factor is heart muscle resistivity and the third physiological factor is skeletal muscle resistivity.

14. The method of claim 6, further comprising:
based on an identification of a third physiological factor of the plurality of physiological factors and third minimally contributing physiological factors of the plurality of physiological factors associated with the third physiological factor, determining a relative change in tissue resistivity corresponding to the third physiological factor based on physiological factors of the plurality of physiological factors other than the third minimally contributing physiological factors, at least some of the difference values, and the determined change in resistivity for the first physiological factor and the second physiological factor, wherein the plurality of vectors further includes a fourth vector and a fifth vector, the fourth vector including a fourth stimulation path extending between the second electrode and the uninsulated portion of the housing and a fourth sense path extending between a third electrode positioned within the ventricle and the uninsulated portion of the housing, and the fifth vector including a fifth stimulation path extending between the first electrode and the uninsulated portion of the housing and a fifth sensing path extending between the first electrode and a fourth electrode positioned along the housing; and
evaluating the relative change in tissue resistivity corresponding to the third physiological factor to determine whether the third physiological factor is an indicator of a medical condition, wherein, for each of the third minimally contributing physiological factors a sensitivity of at least two of the plurality of vectors to the third physiological factor is substantially similar.

15. The method of claim 14, wherein the first physiological factor is blood resistivity, the second physiological factor is heart muscle resistivity and the third physiological factor is skeletal muscle resistivity.

16. The method of claim 6, further comprising:

based on an identification of a third physiological factor of the plurality of physiological factors and third minimally contributing physiological factors of the plurality of physiological factors associated with the third physiological factor, determining a relative change in tissue resistivity corresponding to the third physiological factor based on physiological factors of the plurality of physiological factors other than the third minimally contributing physiological factors, at least some of the difference values, and the determined relative change in tissue resistivity for the first physiological factor and the second physiological factor; and evaluating the relative change in tissue resistivity corresponding to the third physiological factor to determine whether the third physiological factor is an indicator of a medical condition, wherein, for each of the third minimally contributing physiological factors, a sensitivity of at least two of the plurality of vectors to the third physiological factor is substantially similar.

17. The method of claim 16, wherein the first physiological factor is blood resistivity, the second physiological factor is heart muscle resistivity and the third physiological factor is lung volume.

18. The method of claim 12, further comprising:

based on an identification of a fourth physiological factor of the plurality of physiological factors and fourth minimally contributing physiological factors of the plurality of physiological factors associated with the fourth physiological factor, determining a relative change in tissue resistivity corresponding to the fourth physiological factor in response to physiological factors of the plurality of physiological factors other than the fourth minimally contributing physiological factors, at least some of the difference values, and the determined relative change in tissue resistivity for the first physiological factor and the second physiological factor;

based on an identification of a fifth physiological factor of the plurality of physiological factors and fifth minimally contributing physiological factors of the plurality of physiological factors associated with the fifth physiological factor, determining a relative change in tissue resistivity corresponding to the fifth physiological factor in response to physiological factors of the plurality of physiological factors other than the fifth minimally contributing physiological factors, at least some of the difference values, and the determined relative change in tissue resistivity for the first physiological factor, the second physiological factor, the third physiological factor, and the fourth physiological factor, wherein the plurality of vectors include a fifth vector including a fifth stimulation path extending between one of the second electrode and a fourth electrode positioned within an atrium of the heart, and the fourth electrode and the uninsulated portion of the housing, and a fifth sense path extending between one of a fifth electrode positioned within the ventricle and a sixth electrode positioned within the atrium, and the sixth electrode and the uninsulated portion of the housing;

evaluating the relative change in tissue resistivity corresponding to the fourth physiological factor to determine whether the fourth physiological factor is an indicator of a medical condition, wherein, for each of the fourth minimally contributing physiological factors, a sensitivity of at least two of the plurality of vectors to the fifth physiological factor is substantially similar; and evaluating the relative change in tissue resistivity corresponding to the fifth physiological factor to determine whether the fifth physiological factor is an indicator of a medical condition, wherein, for each of the fifth minimally contributing physiological factors, a sensitivity of at least two of the plurality of vectors to the fifth physiological factor is substantially similar.

19. The method of claim 18, wherein the first physiological factor is blood resistivity, the second physiological factor is heart muscle resistivity, the third physiological factor is skeletal muscle resistivity, the fourth physiological factor is lung volume and the fifth physiological factor is heart volume and lung resistivity.

* * * * *